United States Patent [19]
McLees

[11] Patent Number: 4,976,704
[45] Date of Patent: Dec. 11, 1990

[54] MOISTURE DISABLED NEEDLE

[76] Inventor: Donald J. McLees, 2623 Virginia Ave., Everett, Wash. 98201

[21] Appl. No.: 381,092

[22] Filed: Jul. 17, 1989

[51] Int. Cl.⁵ ............................................. A61M 5/32
[52] U.S. Cl. .................................... 604/265; 604/110; 604/272
[58] Field of Search ........ 604/110, 158, 164, 264–266, 604/272

[56] References Cited

U.S. PATENT DOCUMENTS

| | | | | |
|---|---|---|---|---|
| 2,593,980 | 4/1952 | Calicchio | .............................. | 604/265 |
| 2,603,217 | 7/1952 | McShirley | .............................. | 604/265 |
| 3,358,684 | 12/1967 | Marshall | .............................. | 604/272 |
| 4,337,038 | 6/1982 | Saito et al. | .............................. | 433/102 |
| 4,773,901 | 9/1988 | Norton | .............................. | 604/265 |
| 4,781,683 | 11/1988 | Wozniak et al. | .............................. | 604/110 |
| 4,781,703 | 11/1988 | Walker et al. | .............................. | 604/264 |
| 4,798,597 | 1/1989 | Vaillancourt | .............................. | 604/265 |
| 4,846,812 | 7/1989 | Walker et al. | .............................. | 604/265 |
| 4,936,835 | 6/1990 | Haaga | .............................. | 604/265 |

OTHER PUBLICATIONS

Data Sheet-Tafa Series 300-301 Disoluable Metal, Tafa Inc., Concord, NH 03301 Copyright 1989.

*Primary Examiner*—Stephen C. Pellegrino
*Assistant Examiner*—Ralph Lewis

[57] ABSTRACT

A hypodermic needle which is made primarily from a dissolvable material so that after it is used the exposure to moisture causes it to lose its rigid structure and therefore cannot accidentally prick someone and cannot be used again.

4 Claims, 2 Drawing Sheets

MOISTURE DISABLED NEEDLE

BACKGROUND OF THE INVENTION

It would be desirable to have an invention which would help prevent health care workers from becoming infected by hepatitis or AIDS or the like from the accidental needle prick of a contaminated needle. It would also be desirable to have an invention which would help reduce the spread of infectious diseases by preventing drug abusers from re-using contaminated needles.

Several guards for needles have been devised which can help prevent accidental needle pricks after the needle has been used, but most devices are relatively complicated, expensive, and require additional action on the part of the operator beyond the standard procedure. (A mechanism must be pushed or turned, etc.) Any guard which operates entirely automatically can still be violated by a drug abuser.

Another approach is to provide convenient means for destroying needles after they are used. U.S. Pat. No. 3,712,302 shows a flexible needle guard for breaking syringe needles and U.S. Pat. No. 3,893,608 shows a syringe with needle destroying means. In U.S. Pat. No. 3,951,146 disposable self-destructible syringes which render themselves unreuseable are disposed. U.S. Pat. No. 4,027,669 shows a destructible Luer lock syringe and a method of destructing same and U.S. Pat. No. 4,332,323 shows a destructing device for injection needles. All of these mechanisms are relatively complex and add substantially to the cost of a needle or syringe and require additional time or energy on the part of the operator. Also, drug abusers can simply choose not to use the destructive mechanisms or find ways to defeat them.

SUMMARY OF THE INVENTION

Clearly it would be desirable to have a hypodermic needle which is not significantly more costly than a standard needle, which does not have any additional mechanism and therefore does not require any additional action on the part of the operator, and yet one which automatically renders itself harmless and useless after it has been used. Such is the object of this invention.

If a needle were constructed of a material which loses its structural integrity when exposed to moisture, the stated objectives could be met. The needle or needle/-syringe combination could be supplied in a moisture-proof container if need be. When the needle is removed from the container and used, it must necessarily be exposed to moisture, whether the moisture be blood, another body fluid or an injected drug or medication. If the needle were to then dissociate, i.e., disintegrate, dissolve, or otherwise lose its normal physical characteristics, its tip could then no longer accidentally puncture the skin and it could not be re-used.

The material from which the needle is made must exhibit the proper structural characteristics required of a hypodermic needle before it is exposed to moisture and while it is being used without posing a health threat. It is anticipated that different compositions with varying characteristics can have different periods of useful stability for alternate applications. It is conceivable that one variation could be incorporated into a needle used for multiple injections over a period of a few minutes for delivery of a local anesthetic at several locations before being rendered non-functional, while another single use only version could become disabled after one injection.

One material from which a dissolvable needle can be made is currently being offered for commercial applications by TAFA, Inc., of Concord, New Hampshire. It is a proprietary machinable aluminum alloy which rapidly dissolves in water. It is known as alloy 300-301 and has been used commercially as shims for holding internal pipe weldments in place. The shims are inaccessible after the pipe sections have been welded together, but can easily be removed by pumping water through the pipe.

In order to prevent the metal or other material of a dissolvable hypodermic needle from dissociating from the surface during used and remaining behind at withdrawal, it may be necessary to provide the needles with a semi-permeable coating which allows moisture absorption yet contains the disintegrating particles. The coating would act as a barrier to insulate body fluids from the dissolvable structural material and would hold the needle together at withdrawal but would not have enough structural stability of its own after the underlying dissolvable material is exposed to moisture to allow re-penetration. For example the TAFA alloy 300-301 disintegrates into particles of a micron or two across, so a semi-permeable coating having pores of less than a micron could contain the particles while still allowing the passage of liquid molecules.

An optional method for containing the particles would be to electroplate a portion of the needle. Actually only a part of the needle would have to be exposed to moisture to effectively render it no longer useable.

It should be noted that while this description uses the general term hypodermic needle, the dissolvable material could be incorporated into any needle intended for medical purposes, i.e., intravenous catheter needles, blood drawing needles, etc.

DETAILED DESCRIPTION OF THE DRAWINGS

Figure 1:
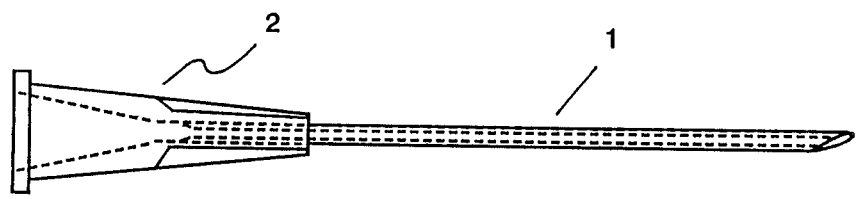
FIG. 1 is a side view showing a typical hypodermic needle.

In FIG. 1 a typical hypodermic needle consisting of the needle 1 and an attached fluid fitting 2 can be seen.

Figure 2:
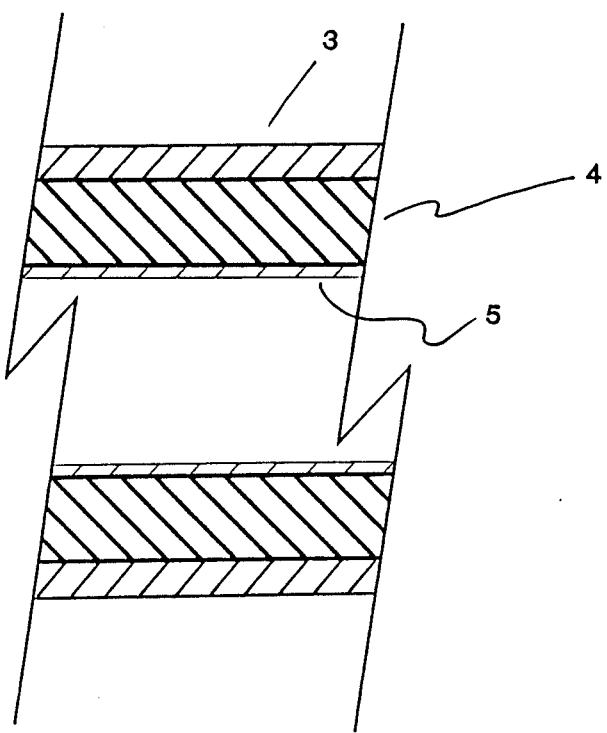
FIG. 2 is a side view cross section of a portion of the inventive needle.

The cross section of FIG. 2 shows a portion of the needle with an optional outer semi-permeable coating 3 which passes moisture but contains dissolving particles of the needle 4, and an inner electroplate layer 5 which can serve as a barrier to block the passing of particles into the fluid inside the needle. For some applications it may be desirable to reverse the position of the coatings, to coat only a portion of the needle, to have only one type of coating, or to not coat the dissolvable material at all.

Figure 3:
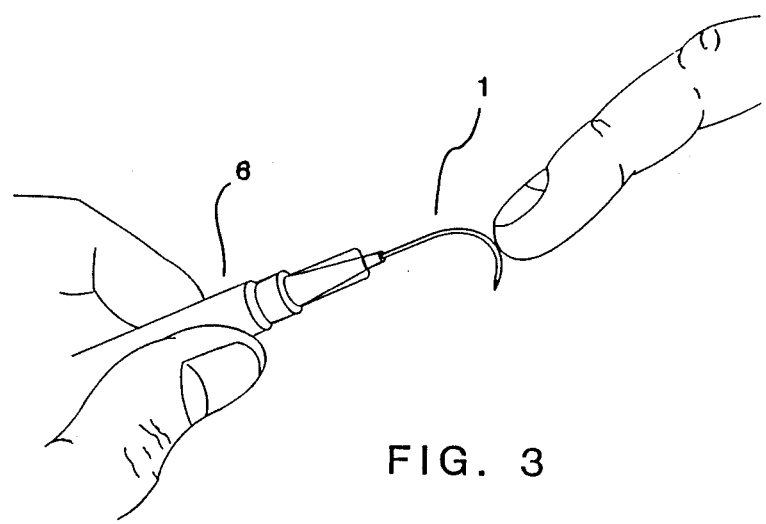
FIG. 3 illustrates a syringe and dissolvable hypodermic needle after use.

FIG. 3 shows the needle 1 disabled after use by moisture and still attached to a typical syringe 6. In this embodiment of the invention the needle has become disabled by the dissolved material but is still held together by the outer semi-permeable membrane.

What is claimed is:

1. A hollow needle for medical purposes made at least in portion of a metal that loses its rigidity upon exposure to moisture such that after use the needle becomes incapable of re-penetrating the skin.

2. A needle as in claim 1 wherein the entire needle is made of the rigidity losing metal.

3. A needle as in claim 1 wherein the metal is an aluminium alloy.

4. A hollow needle for medical purposes made at least in portion of a material that loses its rigidity upon exposure to moisture and further comprising inner and outer surfaces which are coated with semi-permeable membranes that allow the passage of moisture but contain the rigidity losing material.

* * * * *